(12) United States Patent
Bigg et al.

(10) Patent No.: US 6,632,946 B2
(45) Date of Patent: Oct. 14, 2003

(54) TETRACYCLIC ANALOGUES OF CAMPTOTHECINS, THEIR PREPARATION PROCESSES, THEIR USE AS MEDICAMENTS AND THE PHARMACEUTICAL COMPOSITIONS CONTAINING THEM

(75) Inventors: Dennis Bigg, Gif-sur-Yvette (FR); Olivier Lavergne, Palaiseau (FR); Alain Rolland, Palaiseau (FR); Christophe Lanco, Dourdan (FR); Gerard Ulibarri, Bures-sur-Yvette (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/734,167

(22) Filed: Dec. 12, 2000

(65) Prior Publication Data

US 2001/0000521 A1 Apr. 26, 2001

Related U.S. Application Data

(62) Division of application No. 09/582,068, filed as application No. PCT/FR98/02751 on Dec. 16, 1998, now Pat. No. 6,436,951.

(30) Foreign Application Priority Data

Dec. 24, 1997 (FR) .............................. 97 16461

(51) Int. Cl.$^7$ ............................. C07D 213/78
(52) U.S. Cl. ..................................... 546/301
(58) Field of Search .................... 546/71, 301; 514/285

(56) References Cited

FOREIGN PATENT DOCUMENTS

WO         97/22596    *  6/1997

OTHER PUBLICATIONS

STN search 120:191492, p. 42, "Diels–Alder reactions of 4–substituted–2–(1H)–pyridones and hydrolysis of the adducts with acids or bases", Tohoku Coll. Pharm., Sendai, 981 Japan Annu. Rep. Tohoku Coll. Pharm. (1992), 39.*

STN search 106:4801, p. 48, "Synthesis of 3–aromatic ring substituted 2–(4–chlorobenzoylamino)propionic acid derivatives and their antiulcer activities", Tokushim Res. Inst., Otsuka Pharm. Co. , Ltd., Tokushima.*

CA 120:217195, p. 1027, VI. 120, 1994 , Yoon et. al., "Synthesis of 4–[2–[N–[1–methyl–3–(3–carbamylphenyl)propl]amino]ethyl] –1–hydroxy–2–pyridone".*

Chemical Abstracts 120:245564m, "Synthesis and in vitro dopamergic activity of (2–aminoethyl)–1–hydroxy–2–pyridone type dopamine analogs.", Yoon, et. al., vol. 120, 1994, p. 1100.*

Chemcial Abstracts 62:8262b, "Elimination rate and efficiency of atropine in various animal species and individuals", Lendle et al., vol. 62, 1995.*

* cited by examiner

*Primary Examiner*—Alan L. Rotman
*Assistant Examiner*—Binta Robinson
(74) *Attorney, Agent, or Firm*—Muserlian, Lucas and Mercanti

(57) ABSTRACT

The invention relates to new tetracyclic analogues of camptothecin, their preparation processes, their use as medicaments and the pharmaceutical compositions containing them. Said analogues, which include in particular 3-hydroxy-3-(4-oxo-4,6-dihydroindolizino[1,2-b]quinoline-2-yl)pentanoic acid, have a powerful biological activity inhibiting topoisomerase I and/or topoisomerase II.

5 Claims, No Drawings

TETRACYCLIC ANALOGUES OF CAMPTOTHECINS, THEIR PREPARATION PROCESSES, THEIR USE AS MEDICAMENTS AND THE PHARMACEUTICAL COMPOSITIONS CONTAINING THEM

PRIOR APPLICATION

This application is a division of U.S. patent application Ser. No. 09/582,068 filed Jun. 20, 2000, now U.S. Pat. No. 6,436,951 which is a 371 of PCT/FR987/02751 filed Dec. 16, 1998.

Camptothecin is a natural compound which was isolated for the first time from the leaves and bark of the Chinese plant called *camptotheca acuminata* (seer Wall et al., J. Amer. Chem. Soc. 88:3888 (1966)). Camptothecin is a pentacyclic compound, constituted by a an indolizino[1,2-b]quinoline fragment fused with an α-hydroxylactone with six links, and corresponding to the following formula:

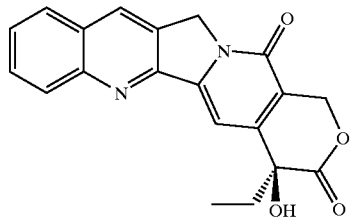

Camptothecin has an anti-proliferative activity in several cancerous cell lines, including the cell lines of human colon, lung and breast tumours (Suffness, M. et al.: The Alkaloids Chemistry and Pharmacology, Bross, A., ed., Vol. 25, p. 73 (Academic Press, 1985)). It has been established that the anti-proliferative activity of camptothecin is related to its inhibitor activity on DNA topoisomerase I.

It had been indicated that α-hydroxylactone was an absolute requirement both for in vivo and in vitro activity of camptothecin (Camptothecins: New Anticancer Agents, Putmesil, M., et al., ed., p. 27 (CRC Press, 1995); Wall, M. et al., Cancer Res. 55:753 (1995); Hertzberg et al., J. Med. Chem. 32:715 (1982) and Crow et al., J. Med. Chem. 35:4160 (1992)). Unexpectedly, the Applicant had discovered that β-hydroxylactones with 7 links have a biological activity which is comparable to or greater than that of α-hydroxylactones (PCT Application No. FR 96/00980). Now, the Applicant has just discovered unexpectedly that certain camptothecin analogues comprising neither α-hydroxylactone nor β-hydroxylactone also present an inhibitory activity on topoisomerases. The present invention therefore relates to a new class of tetracyclic analogues of camptothecin, in which the natural α-hydroxylactone of camptothecin or the β-hydroxylactone of the analogues previously described by the Applicant is absent. The compounds according to the present invention have a powerful biological activity inhibiting topoisomerase I and/or topoisomerase II, which is unexpected with respect to the prior state of the art.

A subject of the invention is therefore compounds of formula (I),

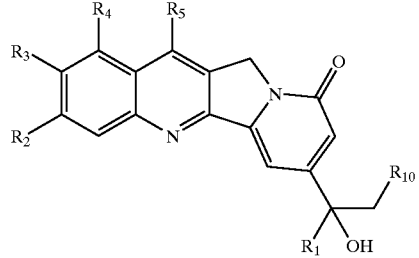

in racemic or enantiomeric form or any combination of these forms, in which $R_1$ represents a lower alkyl, lower alkenyl, lower alkynyl, lower haloalkyl, lower alkoxyalkyl or lower alkylthioalkyl radical;

$R_2$, $R_3$ and $R_4$ represent, independently, an H, hydroxy, lower alkoxy, arylalkoxy, halo, lower haloalkyl, lower alkyl, lower alkenyl, cyano, lower cyanoalkyl, nitro, lower nitroalkyl, amido, lower amidoalkyl, $(CH_2)_m NR_6R_7$, $(CH_2)_m OR_6$, $(CH_2)_m SR_6$, $(CH_2)_m CO_2R_6$, $(CH_2)_m NR_6C(O)R_8$, $(CH_2)_m C(O)R_8$, $(CH_2)_m OC(O)R_8$, $O(CH_2)_m NR_6R_7$, $OC(O)NR_6R_7$, $OC(O)(CH_2)_m CO_2R_6$, aryl or lower arylalkyl radical substituted (i.e., substituted one to four times on the aryl group) or non-substituted, in which the substituent is a lower alkyl, halo, nitro, amino, lower alkylamino, lower haloalkyl, lower hydroxyalkyl, lower alkoxy, or lower alkoxyalkyl) or $R_2$ and $R_3$, or $R_3$ and $R_4$, or $R_4$ and $R_5$, independently form together a chain with 3 or 4 links, in which the elements of the chain are selected from the group consituted by CH, $CH_2$, O, S, N or $NR_9$;

$R_5$ represents an H, halo, lower haloalkyl, lower alkyl, lower alkoxy, lower alkoxyalkyl, lower alkylthioalkyl, cycloalkyl, lower cycloalkylalkyl, cyano, cyanoalkyl, lower alkanesulphonylalkyl, lower hydroxyalkyl, nitro, $(CH_2)_m C(O)R_8$, $(CH_2)_m NR_6C(O)R_8$, $(CH_2)_m NR_6R_7$, $(CH_2)_m N(CH_3)(CH_2)_n NR_6R_7$, $(CH_2)_m OC(O)R_8$, $(CH_2)_m OC(O)NR_6R_7$, aryl or lower arylalkyl radical substituted (i.e. one to four times on the aryl group) or non-substituted, in which the substituent is a lower alkyl, halo, nitro, amino, lower alkylamino, lower haloalkyl, lower hydroxyalkyl, lower alkoxy or lower alkoxyalkyl;

$R_6$ and $R_7$ represent, independently, H, a lower alkyl, lower hydroxyalkyl, lower alkylaminoalkyl, lower aminoalkyl, cycloalkyl, lower cycloalkylalkyl, lower alkenyl, lower alkoxyalkyl, lower haloalkyl, or aryl or lower arylalkyl radical substituted (i.e., one to four times on the aryl group) or non-substituted, in which the substituent is a lower alkyl, halo, nitro, amino, lower alkylamino, lower haloalkyl, lower hydroxyalkyl, lower alkoxy, or lower alkoxyalkyl, or, when the chains $R_6$ and $R_7$ are attached to the same nitrogen atom, $R_6$ and $R_7$ optionally together form an aromatic or non-aromatic heterocycle, for example a heterocycle of morpholine, piperazine or piperidine type, said heterocycle being optionally substituted by one or more groups chosen from the lower alkyl, substituted or non-substituted aryl, substituted or non-substituted arylalkyl, halo, nitro, amino, lower alkylamino, lower haloalkyl, lower hydroxyalkyl, lower alkoxy or lower alkoxyalkyl radicals;

$R_8$ represents an H, lower alkyl, lower hydroxyalkyl, amino, lower alkylamino, lower alkylaminoalkyl, lower aminoalkyl, cycloalkyl, lower cycloalkylalkyl, lower alkenyl, lower alkoxy, lower alkoxyalkyl, lower haloalkyl, or aryl or lower arylalkyl radical substituted (i.e., one to four times on the aryl group) or non-substituted, in which the substituent is a lower alkyl, halo, nitro, amino, lower alkylamino, lower haloalkyl, lower hydroxyalkyl, lower alkoxy, or lower alkoxyalkyl radical;

$R_9$ represents an H, lower alkyl, lower haloalkyl, aryl or arylalkyl radical, the aryl or arylalkyl group optionally being able to be substituted on the aromatic cycle by one or more groups chosen from the lower alkyl, halo, nitro, amino, lower alkylamino, lower haloalkyl, lower hydroxyalkyl, lower alkoxy, or lower alkoxyalkyl radicals;

$R_{10}$ represents a cyano, $C(O)OR_{11}$, 1H-1,2,3,4-tEtrazo-5-yl or 1-alkyl-1,2,3,4-tEtrazo-5-yl radical;

$R_{11}$ represents an H, lower alkyl, lower haloalkyl, lower hydroxyalkyl, alkylcarbonyloxyalkyl, $(CH_2)_p NR_6R_7$, aryl, arylalkyl or aryl radical, the aryl or arylalkyl group optionally being able to be substituted on the aromatic cycle by one or more groups chosen from the lower alkyl, halo, nitro, amino, lower alkylamino, lower haloalkyl, lower hydroxyalkyl, lower alkoxy, or lower alkoxyalkyl radical;

| | |
|---|---|
| m | is an integer comprised between 0 and 6; |
| n | is an integer comprised between 1 and 4; |
| p | is an integer comprised between 2 and 6; | or a pharmaceutically acceptable salt of the latter.

When it is used without further precision, the term alkyl refers to a lower alkyl radical. As used in this text, the term lower with reference to the alkyl, alkylthio and alkoxy groups designates saturated aliphatic hydrocarbon groups, linear or branched, comprising 1 to 6 carbon atoms, such as for example methyl, ethyl, propyl, isopropyl, butyl, t-butyl, methylthio, ethylthio, methoxy and ethoxy. With reference to the alkenyl or alkynyl groups, the term lower designates groups comprising 2 to 6 carbon atoms and one or more double or triple bonds, such as for example the vinyl, allyl, isopropenyl, pentenyl, hexanyl, propenyl ethynyl, propynyl and butynyl groups. The term cycloalkyl designates a cycle of 3 to 7 carbons, such as for example the cyclopropyl, cyclobutyl, cyclopentyl or cyclohexyl groups. The term aryl designates a mono-, di- or tricyclic hydrocarbon compound with at least one aromatic cycle, each cycle containing at most 7 links, such as for example phenyl, naphthyl, anthracyl, biphenyl or indenyl. The term halo means chloro, bromo, iodo or fluoro. The radicals corresponding to the expressions lower haloalkyl, lower cyanoalkyl, lower nitroalkyl, lower amidoalkyl, lower hydrazinoalkyl, lower azidoalkyl, lower arylalkyl, lower hydroxyalkyl, lower alkoxyalkyl, lower alkylthioalkyl, and lower alkanesulphonylalkyl are substituted, respectively, by one to three halo, cyano, nitro, amido, hydrazino, azido, aryl, hydroxy, lower alkoxy, lower alkylthio or lower sulphonyl groups. The lower alkylamino radical can contain one or two lower alkyl groups, and represent for example $NHCH_3$, $NHCH_2CH_3$, $N(CH_3)_2$, or $N(CH_3)(CH_2CH_3)$.

The compounds according to the present invention carry an asymmetric carbon. As a result, the compounds according to the present invention have two possible enantiomeric forms, i.e. in the "R" and "S" configurations. The present invention includes the two enantiomeric forms and all combinations of these forms, including the "RS" racemic mixtures. For the sake of simplicity, when no specific configuration is indicated in the structural formulae, it should be understood that the two enantiomeric forms and their mixtures are represented.

Preferably, a subject of the invention is the compounds of formula (I) as defined above in which $R_1$ represents a lower alkyl radical, $R_2$ represents a hydrogen or halogen atom, $R_3$ represents a hydrogen or halogen atom, a lower alkyl or lower alkoxy radical, $R_4$ represents a hydrogen atom, $R_5$ represents a hydrogen atom or a lower alkyl radical, $R_{10}$ represents a cyano, $C(O)OR_{11}$ or 1H-1,2,3,4-tetrazo-5-yl radical, and finally $R_{11}$ represents an H, lower alkyl, lower haloalkyl, lower hydroxyalkyl, alkylcarbonyloxyalkyl, $(CH_2)_p NR_6R_7$, aryl, arylalkyl or aryl radical, the aryl or arylalkyl group being optionally able to be substituted one the aromatic cycle by one or more groups chosen from the lower alkyl, halo, nitro, amino, lower alkylamino, lower haloalkyl, lower hydroxyalkyl, lower alkoxy, or lower alkoxyalkyl radical; or a pharmaceutically acceptable salt of these compounds.

According to another preferred variant of the invention, $R_1$ represents an ethyl group, $R_2$ represents a hydrogen, chlorine or fluorine atom, $R_3$ represents H, a lower alkyl, halo, or $OR_6$ radical in which $R_6$ represents H, a lower alkyl or lower arylalkyl radical, and preferably H, fluoro, chloro, methyl, methoxy or benzyloxy, $R_4$ represents a hydrogen atom, $R_5$ represents a hydrogen atom or a lower alkyl radical, $R_{10}$ represents a cyano, $C(O)OR_{11}$ or 1H-1,2,3,4-tetrazo-5-yl radical, and finally $R_{11}$ represents an H, lower alkyl, lower haloalkyl, lower hydroxyalkyl, alkylcarbonyloxyalkyl, $(CH_2)_p NR_6R_7$, aryl, arylalkyl or aryl radical, the aryl or arylalkyl group optionally being able to be substituted on the aromatic cycle by one or more groups chosen from the lower alkyl, halo, nitro, amino, lower alkylamino, lower haloalkyl, lower hydroxyalkyl, lower alkoxy, or lower alkoxyalkyl radical.

More particularly, a subject of the invention is the products described below in the examples, and corresponding to the following formulae:

tert-butyl 3-(9-benzyloxy-10-fluoro-4-oxo-4,6-dihydroindolizino [1,2-b]quinoline-2-yl)-3-hydroxypentanoate;

tert-butyl 3-(10-fluoro-9-methoxy-4-oxo-4,6-dihydroindolizino[1,2-b]quinoline-2-yl)-3-hydroxypentanoate;

tert-butyl 3-hydroxy-3-(7-methyl-4-oxo-4,6-dihydroindolizino[1,2-b]quinoline-2-yl)pentanoate;

3-hydroxy-3-(4-oxo-4,6-dihydroindolizino[1,2-b]quinoline-2-yl)pentanitrile;

tert-butyl 3-hydroxy-3-(4-oxo-4,6-dihydroindolizino[1,2-b]quinoline-2-yl)pentanoate;

3-hydroxy-3-(4-oxo-4,6-dihydroindolizino[1,2-b]quinoline-2-yl)pentanoic acid;

3-(9-benzyloxy-10-fluoro-4-oxo-4,6-dihydroindolizino[1,2-b]quinoline-2-yl)-3-hydroxypentanoic acid;

3-(10-fluoro-9-methoxy-4-oxo-4,6-dihydro-indolizino[1,2-b]quinoline-2-yl)-3-hydroxypentanoic acid;

3-hydroxy-3-(7-methyl-4-oxo-4,6-dihydroindolizino[1,2-b]quinoline-2-yl)pentanoic acid;

3-(9-benzyloxy-4-oxo4,6-dihydroindolizino[1,2-b]quinoline-2-yl)-3-hydroxypentanoic acid;

3-(10-chloro-9-methyl-4-oxo-4,6-dihydro-indolizino[1,2-b]quinoline-2-yl)-3-hydroxypentanoic acid;

methyl 3-hydroxy-3-(4-oxo-4,6-dihydroindolizino[1,2-b]quinoline-2-yl)pentanoate;

tert-butylcarbonyloxy-methyl 3-hydroxy-3-(4-oxo-4,6-dihydroindolizino[1,2-b]quinoline-2-yl)pentanoate;

2-[1-hydroxy-1-(1H-1,2,3,4-tetrazo-5-ylmethyl)propyl]-4,6-dihydroindolizino[1,2-b]quinoline-4-one;

or a pharmaceutically acceptable salt of the latter.

For the invention there will be quite particularly preferred 3-hydroxy-3-(4-oxo-4,6-dihydroindolizino[1,2-b]quinoline-2-yl)pentanoic acid or a pharmaceutically acceptable salt of the latter.

A subject of the invention is also a process for the preparation of the compounds of general formula (I) characterized in that a pyridinone of general formula A

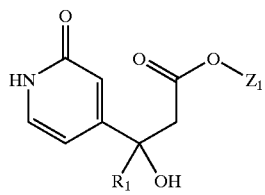

in which $R_1$ has the meaning indicated above and the $Z_1$ group represents a lower alkyl radical, is N-alkylated with a quinoline of general formula B

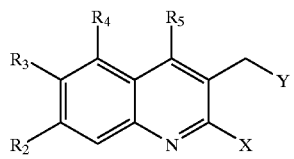

in whiche $R_2$, $R_3$, $R_4$ and $R_5$ have the meaning indicated above, X represents a chlorine, bromine or iodine atom and Y represents either a bromine atom, or a hydroxyl radical, in order to produce the compound of general formula C

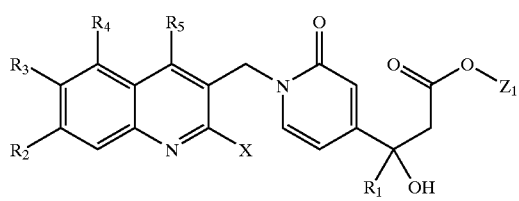

in which $R_1$, $R_2$, $R_3$, $R_4$, $R_5$, $X_1$ and $Z_1$ have the meaning indicated above,
then the compound of general formula C is cyclized in order to obtain the compound of general formula (I) in which $R_1$, $R_2$, $R_3$, $R_4$ and $R_5$ have the meaning indicated above, and $R_{10}$ represents a carbalkoxy radical.

In the above process, the formation of compound C from the compounds of general formula A and B is carried out, when Y represents a hydroxyl function, by a treatment known to a person skilled in the art as Mitsunobu's reaction (see Mitsunobu, O. et al., *Synthesis*, p.1 (1981)). It is necessary for the hydroxyl function of compound B to be displaced by a nucleophile such as compound A, or a deprotonated derivative of the latter, by treatment with a phosphine, for example triphenylphosphine, and an azodicarboxylate derivative, for example diethyl azodicarboxylate, in an aprotic solvent such as, for example, N,N-dimethylformamide or dioxane at a temperature preferably comprised between 0° C. and 60° C. such as, for example, ambient temperature. The formation of compound C from the compounds of general formula A and B, when Y represents a bromine atom, is carried out by treatment of the compound of general formula B by a deprotonated compound of general formula A in an aprotic solvent such as, for example, tetrahydrofuran, dioxane or N,N-dimethylformamide, at a temperature preferably comprised between 0° C. and 30° C. The deprotonation of the compound of general formula A is carried out by treatment with an alkaline alkoxide, an alkaline amide or an alkaline hydride, such as, for example, sodium hydride, in an aprotic solvent such as, for example, tetrahydrofuran, at a temperature preferably comprised between 0° C. and 30° C. Cyclization of compound C is preferably carried out in the presence of a palladium catalyst (for example palladium diacetate) under basic conditions (provided for example by an alkaline acetate optionally combined with a phase transfer agent such as for example tetrabutylammonium bromide), in a solvent such as acetonitrile or amyl alcohol, at a temperature preferably comprised between 50° C. and 120° C. (R. Grigg and coll., *Tetrahedron* 46, page 4003 (1990)).

A subject of the invention is also a process for the preparation of compounds of general formula (I) characterized in that a pyridinone of general formula D

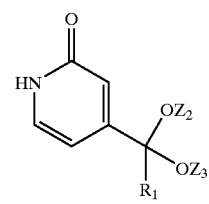

in which $R_1$ has the meaning indicated above and the $Z_2$ and $Z_3$ groups represent, independently, a lower alkyl radical or $Z_2$ and $Z_3$ form together a saturated hydrocarbon chain with 2 to 4 carbons, is N-alkylated with a quinoline of general formula B as defined above in order to produce the compound of general formula E

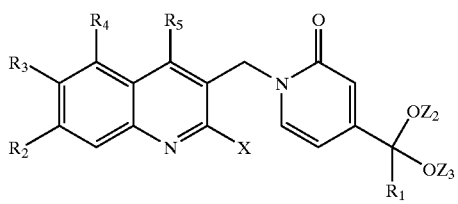

in which $R_1$, $R_2$, $R_3$, $R_4$, $R_5$, X, $Z_2$ and $Z_3$ have the meaning indicated above, then the compound of general formula E is cyclined in order to obtain the compound of general formula F

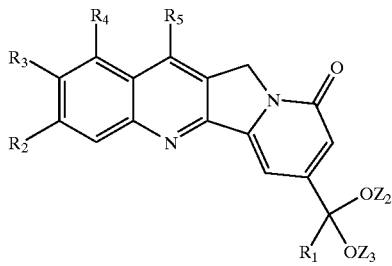

in which $R_1$, $R_2$, $R_3$, $R_4$, $R_5$, $Z_2$ and $Z_3$ have the meaning indicated above,
then the protected carbonyl function of the compounds of general formula F is released in order to produce the compound of general formula G

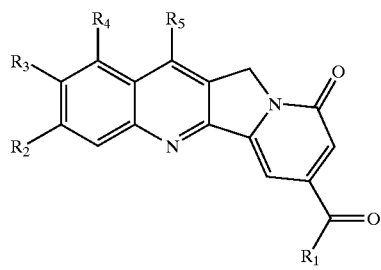

in which $R_1$, $R_2$, $R_3$, $R_4$, and $R_5$ have the meaning indicated above,
then the carbonyl function of the compound of general formula G is treated by an epoxidizing agent in order to produce the compound of general formula H

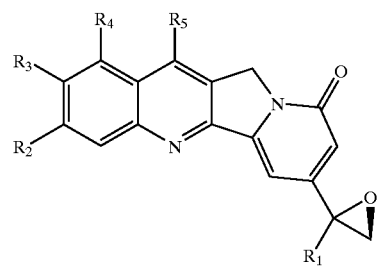

in which $R_1$, $R_2$, $R_3$, $R_4$, and $R_5$ have the meaning indicated above,
then the epoxide of the compound of general formula H is treated with a nitrilating agent in order to produce the compound of general formula (I), in which $R_1$, $R_2$, $R_3$, $R_4$, and $R_5$ have the meaning indicated above, and $R_{10}$ represents a cyano radical.

In the above process, the formation of the compound E from compounds of general formula B and D is carried out, when Y represents a hydroxyl function, by a treatment known to a person skilled in the art under the name of Mitsunobu's reaction (refer to Mitsunobu, O. et al., *Synthesis*, p.1 (1981)). It is necessary for the hydroxyl function of compound B to be displaced by a nucleophile such as compound D, or a deprotonated derivative of the latter, by treatment with a phosphine, for example triphenylphosphine, and an azodicarboxylate derivative, for example diethyl azodicarboxylate, in an aprotic solvent such as, for example, tetrahydrofuran, at a temperature preferably comprised between 0° C. and 60° C., for example at ambient temperature. The formation of compound E from compounds of general formula B and D, when Y represents a bromine atom, is carried out by treatment of the compound of general formula B by a deprotonated compound of general formula D in an aprotic solvent such as, for example, tetrahydrofuran, dioxane or N,N-dimethylformamide, at a temperature preferably comprised between 0° C. and 30° C. The deprotonation of the compound of general formula D is carried out by treatment with an alkaline alkoxide, an alkaline amide or an alkaline hydride, such as, for example, sodium hydride, in an aprotic solvent such as, for example, tetrahydrofuran, at a temperature preferably comprised between 0° C. and 30° C. Cyclization of compound E is preferably carried out in the presence of a palladium catalyst (for example palladium diacetate) under basic conditions (provided for example by an alkaline acetate optionally combined with a phase transfer agent such as for example tetrabutylammonium bromide), in a solvent such as acetonitrile or amyl alcohol, at a temperature preferably comprised between 50° C. and 120° C. (R. Grigg et al., *Tetrahedron* 46, page 4003 (1990)). The release of the protected carbonyl function of the compound of general formula F in order to produce the compound of general formula G is carried out by treatment in acid conditions such as those supplied, for example, by trifluoroacetic acid. The epoxidization producing the compound of general formula H is carried out treating the compound of general formula G with a sulphur ylide, obtained by deprotonation of a trialkylsulphonium salt such as, for example, trimethylsulphonium iodide, by an alkaline alkoxide such as, for example, potassium tert-butylate, in an aprotic polar solvent such as, for example, dimethylsulphoxide, at a temperature preferably comprised between 0° C. and 30° C. The opening of the epoxide of the compound of general formula H in order to produce the compound of general formula (I) in which $R_{10}$ represents a cyano radical is obtained by treatment of the compound of general formula H with a nitrilating agent such as, for example, trimethylsilyl cyanide, in the presence of a Lewis acid such as, for example, diethylaluminium chloride, in an aprotic solvent such as, for example, dichloromethane, at a temperature preferably comprised between 0° C. and 30° C.

A subject of the invention is also a process for the preparation of compounds of general formula (I) characterized in that the carbonyl function of a compound of general formula G as defined above is treated with an appropriate alkylating agent in order to produce the corresponding compound of general formula (I). Said alkylating agent can be provided using reaction conditions known to a person skilled in the art as Reformatsky's reaction. It is necessary to treat a haloacetic ester such as, for example, tert-butyl bromoacetate, or a haloacetonitrile such as, for example, chloroacetonitrile, with a transition metal such as, for example, zinc, in an aprotic solvent such as, for example, tetrahydrofuran at a temperature preferably comprised between 0° C. and 60° C. Said alkylating agent can also be provided by a lithium enolate of an acetic ester such as, for example, tert-butyl acetate treated by lithium diisopropylamidide in an aprotic solvent such as, for example, tetrahydrofuran, at a temperature preferably comprised between −78° C. and ambient temperature.

A subject of the invention is also a process for the preparation of compounds of general formula (I) characterized in that the ester function of a compound of general formula (I) in which $R_{10}$ represents a carbalkoxy radical is hydrolyzed in order to produce a compound of general formula (I) in which $R_{10}$ represents a carboxy radical. This conversion is generally obtained under alkaline conditions provided by an alkaline base such as, for example, lithium hydroxide, in an aqueous polar solvent such as, for example, aqueous methanol or also a tetrahydrofuran/methanol/water mixture. When the ester function of the compound of general formula (I) to be treated is derived from a tertiary alcohol such as, for example, tert-butyl alcohol, saponification can be obtained under acid conditions provided, for example by an aqueous mineral acid such as, for example, hydrochloric acid or sulphuric acid, or also a strong organic acid such as, for example, trifluoroacetic acid.

A subject of the invention is also a process for the preparation of compounds of general formula (I) characterized in that the acid function of a compound of general formula (I) in which $R_{10}$ represents a c y radical is esterified in order to produce a compound of general formula (I) in which $R_{10}$ represents a carbalkoxy radical. Such a conversion is obtained in particular by treatment of the initial carboxylic acid with an appropriate alcohol such as, for example, ethanol, in the presence of an acid catalyst such as, for example, concentrated sulphuric acid or concentrated hydrochloric acid at a temperature preferably comprised between 40° C. and the boiling point of the alcohol in question. The carboxylic acid activated by an agent such as, for example, carbonyldiimidazole or thionyl chloride or dicyclohexylcarbodiimide can also be treated with an alcohol. Finally, there is also included in this esterification process the treatment of the carboxylic group by a base such as, for example, soda or potassium carbonate, in a polar solvent such as, for example, dimethylsulphoxide or N,N-dimethylformamide, followed by an alkylating electrophile such as, for example, methyl iodide or chloromethyl pivaloate.

A further subject of the invention is a process for the preparation of compounds of general formula (I) characterized in that the ester function of a compound of general formula (I) in which $R_{10}$ represents a carbalkoxy radical is transesterified in order to produce a compound of general formula (I) in which $R_{10}$ represents another carbalkoxy radical. Transesterification can be obtained by treatment in the alcohol from which the desired ester is derived, in the presence of acid catalysis provided, for example, by concentrated sulphuric acid or titanium isopropoxide, at a temperature preferably comprised between 40° C. and the reflux temperature of the alcohol in question.

A subject of the invention is also a process for the preparation of compounds of general formula (I) characterized in that the nitrile function of a compound of general formula (I) in which $R_{10}$ represents a cyano radical undergoes a dipolar addition with a nitride in order to produce a compound of general formula (I) in which $R_{10}$ represents a 1,2,3,4-tetrazole-5-yl radical. The latter conversion is obtained by treatment of the cyano compound by a nitride such as, for example, trimethylsilyl nitride, in the presence of a catalyst such as, for example, dibutyltin oxide, in an aprotic solvent such as, for example, toluene, at a temperature preferably comprised between 50° C. and 110° C., for example the reflux temperature of toluene.

In all the processes of the invention described above, the functions carried by the $R_2$, $R_3$, $R_4$ and $R_5$ groups can be protected and deprotected if necessary according to standard protection-deprotection methods known to a person skilled in the art (Greene, T., Protective Groups in Organic Synthesis 10–86 (John Wiley & Sons 1981)). An illustration of this concept of protection-deprotection is given by Example 1 below: the starting product is an aniline of general formula L where $R_3$ is a methoxy radical and the final product corresponds to a compound of general formula (I) where $R_3$ is a benzyloxy radical.

The pyridinones of general formula A are new. They can be prepared according to a process characterized in that a 2-alkoxypyridine of general formula J

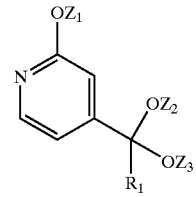

in which $R_1$, $Z_1$, $Z_2$ and $Z_3$ have the meaning indicated above is deprotected in order to produce the pyridinone of general formula K

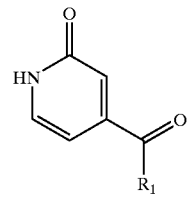

in which $R_1$ has the meaning indicated above;
then the compound of general formula K is treated with a functionalized alkylating agent in order to obtain a compound of general formula A in which $R_1$ and $Z_1$ have the meaning indicated above.

The 2-alkoxypyridines of general formula J can be obtained, for example, according to a process described in Application PCT/FR96/00980. The deprotection of the compounds of general formula J can be obtained either by treatment with a dilute mineral acid such as, for example, normal hydrochloric acid, at a temperature preferably comprised between 60° C. and 120° C. such as, for example, reflux temperature. The deprotection of the compounds of general formula J can also be carried out by treatment with a dealkylating agent such as, for example, boron tribromide or trimethylsilyl iodide (optionally generated in situ), in an aprotic solvent such as, for example, dichloromethane or acetonitrile, at a temperature preferably chosen between 40° C. and 90° C. or, for example, the reflux temperature of the solvent. Treatment of the compound of general formula K with a functionalized alkylating agent can be carried out under reaction conditions known to a person skilled in the art as Reformatsky's reaction. It is necessary to treat a haloacetic ester such as, for example, tert-butyl bromoacetate, or a haloacetonitrile such as, for example, chloroacetonitrile, with a transition metal such as, for example, zinc, in an aprotic solvent such as, for example, tetrahydrofuran at a temperature preferably comprised between 0° C. and 60° C. An appropriate alkylating agent can also be provided by a lithium enolate of an acetic ester such as, for example, tert-butyl acetate treated with lithium diisopropylamidide in an aprotic solvent such as, for example, tetrahydrofuran, at a temperature preferably comprised between −78° C. and ambient temperature.

The pyridinones of general formula D are new. They can be obtained according to a process characterized in that the ketonic function is protected in the compound of general formula K in order to obtain a compound of general formula D in which $R_1$, $Z_2$ and $Z_3$ have the meaning indicated above. Such a protection obtained under standard reaction conditions and known to a person skilled in the art as acetalization (Greene, T., protective Groups in Organic Synthesis 10–86 (John Wiley & Sons 1981)).

The quinolines of general formula B can be obtained from anilines of general formula L

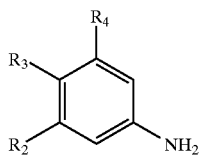

in which $R_2$, $R_3$ and $R_4$ have the meaning indicated in the general formulae of compounds (I), or also are precursors of the latter in the context of the use of protection-deprotection techniques. In this way, in the processes below, the $R_2$, $R_3$ and $R_4$ groups can be protected if necessary according to standard protection methods (Greene, T., Protective Groups in Organic Synthesis 10–86 (John Wiley & Sons 1981)). An illustration of this concept of protection-deprotection is given by Example 1 below: the starting product is an aniline of formula L where $R_3$ is a methoxy radical and the final product corresponds to a compound of formula (I) where $R_3$ is a benzyloxy radical.

The quinolines of formula B can be obtained according to the following process: the anilines of general formula L as defined above are N-acetylated by treatment with an acetylating agent such as, for example, acetic anhydride. The acetanilides obtained in this way are treated at a temperature preferably comprised between 50° C. and 100° C., more preferentially at 75° C., with a reagent known to a person skilled in the art as Vilsmeyer's reagent (obtained by the action of phosphoryl oxychloride on N,N-dimethylformamide at a temperature preferably comprised between 0° C. and 10° C.) in order to produce the corresponding 2-chloro-3-quinolinecarbaldehyde (refer, for example, to Meth-Cohn, et al. *J. Chem. Soc., Perkin Trans. I* p.1520 (1981); Meth-Cohn, et al. *J. Chem. Soc., Perkin Trans. I* p.2509 (1981); and Nakasimhan et al. *J. Am. Chem. Soc.*, 112, p.4431 (1990)). The chlorine in position 2 of the 2-chloro-3-quinolinecarbaldehydes can be substituted by iodine or bromine by heating the product in an inert solvent such as, for example, acetonitrile in the presence of an iodine or bromine salt (for example sodium iodide or tetrabutylammonium bromide). A trace of acid such as concentrated hydrochloric acid may be necessary in order to catalyze this conversion. The 2-halo-3-quinolinecarbaldehydes are easily reduced to the corresponding 2-halo-3-quinolinemethanols of general formula B where Y represents a hydroxyl function, under standard conditions known to a person skilled in the art such as treatment in an alcoholic solvent (for example methanol) with sodium borohydride at a temperature preferably comprised between 0° C. and 4° C. The 2-halo-3-quinolinemethanols of general formula B where Y represents a hydroxyl function can be converted into 3-bromomethyl-2-haloquinolines of general formula B where Y represents a bromine atom by treatment with tetrabromomethane in the presence of a phosphine such as, for example, triphenylphosphine, in a chlorinated aprotic solvent such as, for example, dichloromethane or 1,2-dichloroethane at ambient temperature.

The quinolines of formula B can also be obtained according to the following process: the anilines of general formula L as defined above are acylated by reaction with a nitrile (such as chloroacetonitrile or propionitrile) in the presence of boron trichloride and of another Lewis acid such as aluminium trichloride, titanium tetrachloride or diethylaluminium chloride in an aprotic solvent or a mixture of aprotic solvents, followed by hydrolysis (cf Sugasawa, T, et al. *J Am. Chem. Soc.* 100, p. 4842 (1978)). The intermediate obtained in this way is then treated with ethylmalonyl chloride in an aprotic solvent such as acetonitrile in the presence of a base such as triethylamine, then treated with an alkaline alcoholate, for example sodium ethylate in ethanol, in order to produce ethyl 2-hydroxy-3-quinolinecarboxylate substituted in position 4. The latter is converted into ethyl 2-chloro-3-quinolinecarboxylate by treatment with phosphoryl oxychloride. When position 4 of the quinoline carries a chloromethyl group, a nucleophilic substitution can be carried out by treatment with a secondary amine such as for example dimethylamine, N-methylpiperazine, morpholine or piperidine. The ethyl 2-chloro-3-quinolinecarboxylate is then reduced by diisobutylaluminium hydride in an aprotic solvent such as dichloromethane in order to produce 2-chloro-3-quinolinemethanol of general formula B. Analogues of the intermediate quinolines B have been described in the literature and in particular in PCT Application No. 95/05427.

A subject of the invention is also, as new industrial products, and in particular as new industrial products intended for the preparation of the products of general formula (I), the products of formulae A, D and K as described above.

Certain compounds of the invention can be prepared in the form of pharmaceutically acceptable salts according to the usual methodes. Acceptable salts include, as a non-limitative example, the addition salts of inorganic acids such as hydrochloride, sulphate, phosphate, diphosphate, hydrobromide and nitrate or those of inorganic acids such as acetate, maleate, fumarate, tartarate, succinate, citrate, lactate, methane sulphonate, p-toluenesulphonate, pamoate, salicylate, oxalate and stearate. The salts formed from bases such as sodium or potassium hydroxide also fall within the field of application of the present invention, when they can be used. For other examples of pharmaceutically acceptable salts, reference can be made to "Pharmaceutical Salts", F. M. Berge, *J. Pharm. Sci.* 66:1 (1977).

The compounds of the present invention have useful pharmacological properties. In this way the compounds of the present invention have an inhibitory activity on topoisomerase I and/or an inhibitory activity on topoisomerase II. The state of the art suggests that the compounds of the invention have an anti-tumoral activity, an anti-parasitic activity and an anti-viral activity. The compounds of the present invention can in this way be used in different therapeutic applications.

There follows in the experimental part an illustration of the pharmacological properties of the compounds of the invention.

The compounds can inhibit the topoisomerases of type I and/or of type II, in a patient, for example a mammal such as man, by administration to this patient of a therapeutically effective quantity of a compound of general formula (I).

The compounds of the invention also have an anti-tumoral activity. They can be used for the treatment of tumours, for example of tumours expressing a topoisomerase, in a patient by administration to the latter of a therapeutically effective quantity of a compound of general formula (I). Examples of tumours or of cancers include cancers of the oesophagus, the stomach, the intestines, the rectum, the oral cavity, the pharynx, the larynx, the lung, the colon, the breast, the cervix uteri, the corpus endometrium, the ovaries, the prostate, the testes, the bladder, the kidneys, the liver, the pancreas, the bones, the conjunctive tissues, the skin, the eyes, the brain and the central nervous system, as well as cancer of the thyroid gland, leukaemia, Hodgkin's disease, lymphomas other than Hodgkin's, multiple myelomas and others.

They can also be used for the treatment of parasitic infections by inhibition of the hemoflagellates (for example in trypanosomiasis or infections of leishmania type) or by inhibition of plasmodia (such as for example in malaria), but also for the treatment of viral infections or diseases.

These properties make the products of general formula (I) suitable for pharmaceutical use. A subject of the present Application is therefore also, as medicaments, the compounds of general formula (I) as defined above, as well as the addition salts with pharmaceutically acceptable mineral or organic acids of products of general formula (I), as well as pharmaceutical compositions containing at least one of the compounds as defined above as active ingredient.

The invention thus relates to pharmaceutical compositions containing a compound of general formula (I) as defined previously or a pharmaceutically acceptable salt of the latter, combined with a pharmaceutically acceptable carrier chosen according to the administration mode (for example oral, intravenous, intraperitoneal, intramuscular, trans-dermic or sub-cutaneous administration). The pharmaceutical composition (for example therapeutic) can be in solid or liquid form, or in the form of liposomes or of lipidic micells.

The pharmaceutical composition can be in a solid form such as, for example, powders, pills, granules, tablets, liposomes, capsules or suppositories. The pill, tablet or capsule can be coated with a substance capable of protecting the composition from the action of gastric acid or enzymes in the subject's stomach for a sufficient length of time to allow the composition to pass undigested into the subject's small intestine. The compound can also be administered locally, for example at the very point where the tumour is located. The compound can also be administered according to the sustained release process (for example a sustained release composition or an infusion pump). The appropriate solid carriers can be, for example, calcium phosphate, magnesium stearate, magnesium carbonate, talc, sugars, lactose, dextrine, starch, gelatin, cellulose, methyl cellulose, sodium carboxymethyl cellulose, polyvinylpyrrolidine and wax. The pharmaceutical compositions containing a compound of the invention can therefore also be presented in liquid form such as, for example, solutions, emulsions, suspensions or a sustained release formulation. The appropriate liquid carriers can be, for example, water, organic solvents such as glycerol or glycols such as polyethylene glycol, as well as their mixtures, in varying proportions, in water.

A subject of the invention is also the use of the products of formula (I) as defined above, for the preparation of medicaments intended to inhibit topoisomerases, and more particularly to inhibit the topoisomerases of type I, or the topoisomerases of type II, or, simultaneously, the two types of topoisomerase, for the preparation of medicaments intended to treat tumours, for the preparation of medicaments intended to treat parasitic infections, as well as for the preparation of medicaments intended to treat viral infections or diseases.

The dose of a compound according to the present invention, to be allowed for the treatment of the diseases or disorders mentioned above, varies according to the administration mode, the age and body weight of the subject to be treated as well as the subject's state, and it will definitively be decided by the attending doctor or veterinary surgeon. Such a quantity determined by the attending doctor or veterinary surgeon is here called "effective therapeutic quantity".

Unless defined differently, all the technical and scientific terms used here have the same meaning as that normally understood by an ordinary specialist in the field to which this invention belongs. Similarly, all the publications, patent applications, patents and any other references mentioned here are included by way of reference.

EXPERIMENTAL PART

Example 1 tert-Butyl 3-(9-Benzyloxy-10-fluoro-4-oxo-4,6-dihydroindolizino[1,2-b]quinoline-2-yl)-3-hydroxypentanoate 1.a. N-(3-Fluoro-4-methoxyphenyl)acetamide:

A mixture of 3-fluoro-4-methoxyaniline (56.4 g; 400 mmol) and triethylamine (56 ml; 400 mmol) in dichloromethane (400 ml) is cooled down using an ice bath. Acetic anhydride (57 ml; 600 mmol) is added dropwise and the reaction mixture is agitated for 3 hours at ambient temperature. The reaction medium is then washed successively with water, with an aqueous solution of 10% sodium bicarbonate then with an aqueous solution saturated in sodium chloride. The organic fraction is dried over sodium sulphate and concentrated under reduced pressure. The residue is recrystallized from an ethyl acetate/pentane mixture in order to produce 66.5 g (91%) of a white solid, m.p. 120° C.

NMR $^1$H (CDCl$_3$): 2.15 (s, 3H); 3.86 (s, 3H); 6.92 (dd, 1H); 7.13 (dd, 1H); 7.40 (dd, 1H); 7.55 (br, 1H).

1.b. 2-Chloro-7-fluoro-6-methoxy-3-quinolinecarbaldehyde:

N-(3-fluoro-4-methoxyphenyl)acetamide (obtained according to 1.a, 30 g, 164 mmol) is added to Vilsmeyer's reagent (obtained, under an argon atmosphere, by adding phosphoryl oxychloride (75 ml, 800 mmol) dropwise to anhydrous N,N-dimethylformamide (25 ml, 320 mmol) cooled down with an ice bath, then agitated for 0.5 hours) and the resulting mixture is heated at 75° C. for 2 hours. After cooling down to ambient temperature, the reaction medium is added dropwise to a mixture of ice and water (500 ml). The yellow suspension obtained in this way is maintained under agitation for 1 hour. The precipitate obtained is then filtered, washed with water to a neutral pH then dried under reduced pressure in the presence of phosphorus pentoxide in order to produce 13.6 g (35%) of a beige solid, m.p. 180° C.

NMR $^1$H (DMSO): 4.05 (s, 3H); 7.30 (d, 1H); 7.74 (d, 1H); 8.16 (s, 1H); 10.52 (s, 1H).

1.c. 2-Chloro-7-fluoro-6-hydoxy-3-quinolinecarbaldehyde:

2-chloro-7-fluoro-6-methoxy-3-quinolinecarbaldehyde (obtained according to 1.b, 27.2 g, 113 mmol) in suspension in anhydrous dichloromethane (980 ml) is treated dropwise with boron tribromide (molar solution in dichloromethane, 340 ml, 340 mmol) and the resulting mixture is agitated at ambient temperature for 24 hours then cooled down to 0° C. The reaction medium is added dropwise to a water/ice mixture (500 ml) under agitation, the solid formed is filtered then dried under reduced pressure in order to produce a yellow solid (13.5 g, 53%), m.p. 270° C.

NMR $^1$H (DMSO): 7.64 (d, 1H); 7.84 (d, 1H); 8.84 (s, 1H); 10.33 (s, 1H); 11.15 (s, 1H).

1.d. 6-Benzyloxy-2-chloro-7-fluoro-3-quinolinecarbaldehyde:

Potassium carbonate (9.2g, 66 mmol) is added to a solution of 2-chloro-7-fluoro-6-hydoxy-3-quinolinecarbaldehyde (obtained according to 1.c, 13 g, 58 mmol) in anhydrous N,N-dimethylformamide (120 ml) and the mixture, placed under an argon atmosphere, is cooled down to 0° C. Benzyl bromide (7.9 ml, 66 mmol) is added dropwise and the reaction medium is maintained under agitation at ambient temperature for 16 hours. The reaction medium is then poured into ice cold water (200 ml) and the resulting yellow solid is filtered, then taken up in ethanol (200 ml) and concentrated under reduced pressure. The residue is taken up in ethyl ether (200 ml) and the resulting yellow solid is filtered then dried under reduced pressure in order to produce 15 g (82%) of a yellow solid, m.p. 228° C.

NMR $^1$H (CDCl$_3$): 5.29 (s, 2H); 7,2–7.6 (m, 6H); 7.72 (d, 1H); 8.60 (s, 1H); 10.52 (s, 1H).

1.e. 6-Benzyloxy-7-fluoro-2-iodo-3-quinolinecarbaldehyde:

A suspension of 6-benzyloxy-2-chloro-7-fluoro-3-quinolinecarbaldehyde (obtained according to 1.d, 15 g, 47 mmol) and sodium iodide (18 g, 120 mmol) in anhydrous acetonitrile (500 ml) is treated with a catalytic quantity of concentrated hydrochloric acid (1.2 ml), then taken to reflux under argon for 8 hours. The reaction mixture is then concentrated to 20% of the initial volume, then treated with a 10% aqueous solution of sodium bicarbonate to a neutral pH, then filtered and washed successively with water, ethanol and ethyl ether in order to produce 13 g (68%) of a yellow solid, m.p. 210° C.

NMR $^1$H (CDCl$_3$): 5.28 (s, 2H); 7.43 (d, 1H); 7.43 (m, 5H); 7.74 (d, 1H); 8.39 (s, 1H); 10.21 (s, 1H).

1.f 6-Benzyloxy-7-fluoro-2-iodo-3-quinolylmethanol:

A suspension of 6-benzyloxy-7-fluoro-2-iodo-3-quinolinecarbaldehyde (obtained according to i.e, 13 g, 32 mmol) in methanol (100 ml) is treated with sodium borohydride (1.85 g, 48 mmol). After 1 hour of reaction, the reaction medium is concentrated under reduced pressure then taken up with water, filtered, washed with water and ethanol in order to produce, after drying under reduced pressure, 10 g (76%) of a white solid, m.p. 188° C.

NMR $^1$H (CDCl$_3$): 4.61 (d, 2H); 5.19 (s, 2H); 5.32 (t, 1H); 7.21 (d, 1H); 7.62 (d, 1H); 8.09 (s, 1H).

1.g. 1-(2-oxo-1,2-Dihydro-4-pyridinyl)-1-propanone:

A mixture of 4-(2-ethyl-1,3-dioxan-2-yl)-2-methoxypyridine (prepared according to the method described in the Patent Application PCT/FR96/00980, 57 g, 255 mmol) and sodium iodide (88 g, 580 mmol) in acetonitrile (1 1) is treated with trimethylsilane chloride (74 ml, 586 mmol), taken to reflux for 3 hours, then agitated at ambient temperature for 16 hours. The reaction medium is then treated with water (100 ml) and concentrated to dryness after elimination of the insolubles by filtration. The residue is taken up in ethyl acetate and washed successively with water and with an aqueous solution saturated in sodium chloride. The organic phase is dried, concentrated under reduced pressure, and the residue is taken up in diethyl ether in order to produce after filtration and drying 30 g (88%) of a white solid, m.p. 168° C.

NMR $^1$H (CDCl$_3$): 1.22 (t, 3H); 2.96 (q, 2H); 6.88 (d, 1H); 7.05 (s, 1H); 7.49 (d, 1H); 13.2 (br, 1H).

1.h. tert-Butyl 3-Hydroxy-3-(2-oxo-1,2-dihydro-4-pyridinyl)pentanoate:

A solution of diisopropylamine (35 ml, 250 mmol) in anhydrous tetrahydrofuran (275 ml) is treated dropwise at 0° C., under argon, with n-butyllithium (2.5 M in hexane, 100 ml, 250 mmol). The resulting mixture is agitated at 0° C. for 15 min, then cooled down to −78° C. and treated with tert-butyl acetate (33.8 ml, 250 mmol). After agitation at −78° C. for 15 min, the resulting lithiated reagent is added dropwise, over 1 hour, using a transfer canula, to a solution of 1-(2-oxo-1,2-dihydro-4-pyridinyl)-1-propanone (obtained according to 1.g, 15.2 g, 100 mmol) at −78° C. in anhydrous tetrahydrofuran (330 ml) and the resulting mixture is maintained at −78° C. for 15 min, then allowed to return to 0° C. for 1 hour. The reaction medium is hydrolyzed by the addition of water (60 ml) then the volatiles are evaporated off under reduced pressure. The residue is taken up in ethyl acetate and the resulting solution is washed with water, dried and concentrated. The residue is suspended in diethyl ether and filtered in order to produce after drying 21.5 g (80%) of a white solid, m.p. 167° C.

NMR $^1$H (DMSO): 0.67 (t, 3H); 1.25 (s, 9H); 1.70 (q, 2H); 2.59 (dd, 2H); 4.97 (s, 1H); 6.18 (d, 1H); 6.32 (s, 1H); 7.23 (d, 1H); 11.3 (br, 1H).

1.i. tert-Butyl 3-[1-(6-Benzyloxy-7-fluoro-2-iodo-3-quinolylmethyl)-2-oxo-1,2-dihydro-4-pyridinyl]-3-hydroxypentanoate:

A mixture, under an argon atmosphere, of 6-benzyloxy-7-fluoro-2-iodo- 3-quinolylmethanol (obtained according to 1.f, 2.05 g, 5 mmol), tert-butyl 3-hydroxy-3-(2-oxo-1,2-dihydro-4-pyridinyl)pentanoate (obtained according to 1.h, 1.47 g, 5.5 mmol), and tributylphosphine (1.36 ml, 5.5 mmol) in anhydrous tetrahydrofuran (20 ml) is treated dropwise with diethyl azodicarboxylate (1.3 ml, 7.5 mmol). The reaction mixture is then agitated at ambient temperature for 6 hours, then concentrated under reduced pressure. The resulting oily residue is taken up in dichloromethane (100 ml) and washed with saturated aqueous ammonium chloride then with saturated aqueous sodium chloride. The organic phase is dried over sodium sulphate then concentrated to 5 ml and acetonitrile is added in order to obtain a white precipitate which is kept at 4° C. for 16 hours. The precipitate is collected by filtration then washed with isopropyl ether in order to produce 1.8 g (55%) of a white solid, m.p. 174° C.

NMR $^1$H (DMSO): 0.73 (t, 3H); 1.27 (s, 9H); 1.78 (m, 2H); 2.67 (dd, 2H); 5.12 (s, 2H); 5.26 (s, 2H); 6.40 (d, 1H); 6.52 (s, 1H); 7,3–7.6 (m, 7H); 7.72 (m, 1H); 7.86 (m, 1H).

1.j. tert-Butyl 3-(9-Benzyloxy-10-fluoro-4-oxo-4,6-dihydroindolizino[1,2-b]quinoline-2-yl)-3-hydroxypentanoate:

A mixture of tert-butyl 3-[1-(6-benzyloxy-7-fluoro-2-iodo-3-quinolylmethyl)-2-oxo-1,2-dihydro-4-pyridinyl]-3-hydroxypentanoate (obtained according to 1.i, 1.6 g, 2.4 mmol), tetrabutylammonium bromide (0.77 g, 2.4 mmol), potassium acetate (0.24 ml, 2.4 mmol) and palladium acetate (0.55 g, 2.4 mmol) in anhydrous amyl alcohol (30 ml) is heated at 80° C. under an argon atmosphere for 3 hours, then concentrated under reduced pressure. The residue is taken up in methanol (50 ml) and dichloromethane (100 ml), filtered through celite then concentrated under reduced pressure in order to produce a pink solid which is taken up in methanol, then treated with hot activated carbon. The liquor obtained by filtration is concentrated to 5 ml, then placed at 4° C. for 16 hours. The resulting precipitate is collected by filtration and washed with diethyl ether in order to produce, after drying, 370 mg (29%) of a white solid, m.p. >275° C.

NMR $^1$H (DMSO): 0.73 (t, 3H); 1.22 (s, 9H); 1.83 (m, 2H); 2.77 (dd, 2H); 5.21 (s, 2H); 5.25 (s, 1H); 5.37 (s, 2H); 6.59 (s, 1H); 7.21 (s, 1H); 7,4–7.5 (m, 3H); 7.57 (d, 2H); 7.88 (d, 1H); 7.95 (d, 1H); 8.56 (s, 1H).

Example 2 tert-Butyl 3-(10-Fluoro-9-methoxy-4-oxo-4,6-dihydroindolizino[1,2-b]quinoline-2-yl)-3-hydroxypentanoate Procedures i.e, 1.f, 1.i and 1.j are applied starting with 2-chloro-7-fluoro-6-methoxy-3-quinolinecarbaldehyde (obtained according to 1.b) instead of 6-benzyloxy-2-chloro-7-fluoro-3-quinoline-carbaldehyde. A white solid is obtained; m.p. 247° C.

NMR $^1$H (DMSO): 0.72 (t, 3H); 1.22 (s, 9H); 1.85 (m, 2H); 2.77 (dd, 2H); 4.02 (s, 3H); 5.20 (s, 2H); 5.27 (s, 1H); 6.59 (s, 1H); 7.20 (s, 1H); 7.73 (d, 1H); 7.91 (d, 1H); (s, 1H).

Example 3 tert-Butyl 3-Hydroxy-3-(7-methyl-4-oxo-4,6-dihydroindolizino[1,2-b]quinoline-2-yl)pentanoate 3.a. Ethyl 4-Methyl-2-oxo-1,2-dihydro-3-quinolinecarboxylate:

A solution of ethylmalonyl chloride (12.9 ml, 100 mmol) in anhydrous acetonitrile (30 ml) is added dropwise to a solution of 2-aminoacetophenone (10.5 g, 78 mmol) and triethylamine (13.9 ml, 100 mmol) in anhydrous acetonitrile (10 ml), under argon and at 0° C. The reaction medium is heated up to ambient temperature then treated dropwise and under argon with a solution of sodium ethylate (obtained with 1.8 g, 78 mmol, of sodium in 80 ml of ethanol), then left under agitation for 12 hours at ambient temperature. The reaction mixture is then poured into ice cold water (100 ml) and agitated for two hours, then filtered. The precipitate collected in this way is washed with water, with ethanol and with ether in order to produce 15.2 g (84%) of a white solid.

NMR $^1$H (DMSO): 1.30 (t, 31H); 2.40 (s, 3H); 4.31 (q, 2H); 7.24 (t, 1H); 7.37 (d, 1H); 7.4 (br, 1H); 7.58 (t, 1H); 7.81 (d, 1H).

3.b. Ethyl 2-Chloro-4-methyl-3-quinolinecarboxylate:

A suspension of ethyl 4-methyl-2-oxo-1,2-dihydro-3-quinolinecarboxylate (obtained according to 3.a, 15.2 g, 0.066 mol) in phosphoryl chloride (243 ml) is taken to reflux for 6 hours. The phosphoryl chloride is evaporated under reduced pressure without taking to dryness, and the viscous residue is poured into ice cold water (300 ml). The precipitate obtained in this way is filtered, washed with water to a neutral pH, then washed with ethanol and with diethyl ether in order to produce after drying 8.8 g (53%) of a white solid, m.p. 110° C.

NMR $^1$H (CDCl$_3$): 1.45 (t, 3H); 2.67 (s, 3H); 4.51 (q, 2H); 7.61 (t, 1H); 7.76 (t, 1H); 8.00 (m, 2H).

3.c. 2-Chloro-4-methyl-3-quinolinemethanol:

A solution under argon of ethyl 2-chloro-4-methyl-3-quinolinecarboxylate (obtained according to 3.b, 8.75 g, 35 mmol) in anhydrous dichloromethane (200 ml) is treated dropwise, at ambient temperature, with diisobutylaluminium hydride (1M in dichloromethane, 65 ml, 65 mmol), then heated at 40° C. for 4 hours. The reaction medium is then cooled down to 0° C., then cautiously treated with a 20% aqueous solution of Rochelle salt (105 ml) and dichloromethane (200 ml) and maintained under agitation for 1 hour. The organic phase is then decanted, washed three times with water, then dried over magnesium sulphate and concentrated under reduced pressure. The residue is purified by column chromatography (SiO$_2$, ethyl acetate/heptane: 5/95 to 50/50) in order to produce 6 g (82%) of a white solid.

NMR $^1$H (CDCl$_3$): 2.24 (br, 1H); 2.81 (s, 3H); 5.04 (d, 2H); 7.58 (t, 1H); 7.71 (t, 1H); 7.99 (m, 2H).

3.d. tert-Butyl 3-[1-(2-Chloro-4-methyl-3-quinolylmethyl)-2-oxo-1,2-dihydro-4-pyridinyl]-3-hydroxypentanoate:

A mixture, under an argon atmosphere, of 2-chloro-4-methyl-3-quinolinemethanol (obtained according to 3.c, 2.08 g, 10 mmol), of tert-butyl 3-hydroxy-3-(2-oxo-1,2-dihydro-4-pyridinyl)pentanoate (obtained according to 1.h, 2 g, 11 mmol), and tributylphosphine (2.75 ml, 11 mmol) in anhydrous tetrahydrofuran (40 ml) is treated dropwise with diethyl azodicarboxylate (2.6 ml, 15 mmol). The reaction mixture is then agitated at ambient temperature for 6 hours, then concentrated under reduced pressure. The resulting oily residue is taken up in dichloromethane (200 ml) and washed with saturated aqueous ammonium chloride then with saturated aqueous sodium chloride. The organic phase is dried over sodium sulphate then concentrated to 5 ml and acetonitrile is added in order to obtain a white precipitate which is kept at 4° C. for 16 hours. The precipitate is collected by filtration then washed with isopropyl ether in order to produce 1.8 g (39%) of a white solid.

NMR $^1$H (DMSO): 0.73 (t, 3H); 1.28 (s, 9H); 1.75 (q, 2H); 2.66 (dd, 2H); 2.80 (s, 3H); 5.11 (s, 1H); 5.44 (dd, 2H); 6.29 (d, 1H); 6.49 (s, 1H); 6.70 (s, 1H); 7.29 (d, 1H); 7.80 (t, 1H); 7.96 (t, 1H); 8.05 (d, 1H); 8.32 (d, 1H).

3.e. tert-Butyl 3-Hydroxy-3-(7-methyl-4-oxo-4,6-dihydroindolizino[1,2-b]quinoline-2-yl)pentanoate:

A mixture of tert-butyl 3-[1-(2-chloro-4-methyl-3-quinolylmethyl)-2-oxo-1,2-dihydro-4-pyridinyl]-3-hydroxypentanoate (obtained according to 3.d, 1.29 g, 2.8 mmol), tetrabutylammonium bromide (0.99 g, 3.1 mmol), potassium acetate (0.41 g, 4.2 mmol) and palladium acetate (0.69 g, 3.1 mmol) in anhydrous amyl alcohol (30 ml) is heated at 80° C. under an argon atmosphere for 2 hours, then filtered while warm and concentrated under reduced pressure. The residue is purified by column chromatography (SiO$_2$, methanol/dichloromethane: 5/95) in order to produce 370 mg (31%) of a white solid, m.p. >275° C.

NMR $^1$H (DMSO): 0.73 (t, 3H); 1.21 (s, 9H); 1.86 (m, 2H); 2.77 (s, 3H); 2.77 (dd, 2H); 5.23 (s, 2H); 5.26 (s, 1H); 6.61 (s, 1H); 7.25 (s, 1H); 7.71 (t, 1H); 7.84 (t, 1H); 8.13 (d, 1H); 8.24 (d, 1H).

Example 4

3-Hydroxy-3-(4-oxo-4,6-dihydroindolizino[1,2-b]quinoline-2-yl)pentanitrile 4.a. 2-Chloro-3-quinolylmethanol:

A suspension of 2-chloro-3-quinolinecarbaldehyde (19.2 g, 100 mmol) in methanol (400 ml) is treated with sodium borohydride (5.7 g, 150 mmol). After agitation for 2 hours at ambient temperature, the reaction medium is concentrated under reduced pressure then taken up in water, filtered, washed with water and with ethanol in order to produce, after drying under reduced pressure, 15.8 g (81%) of a white solid, m.p. 166° C.

NMR $^1$H (DMSO): 4.70 (s, 2H); 5.96 (br, 1H); 7,5–8.2 (m, 4H); 8.48 (s, 1H).

4.b. 3-Bromomethyl-2-chloroquinoline:

A solution under argon of 2-chloro-3-quinolylmethanol (obtained according to 4.a, 15.5 g 80 mmol) and triphenylphosphine (32 g, 120 mmol) is treated with small portions of tetrabromomethane (40 g, 120 mmol) while keeping the temperature of the reaction medium below 30° C. After agitation under argon for 2 hours at ambient temperature, the reaction medium is concentrated under reduced pressure, and the residue is purified by column chromatography (SiO$_2$, ethyl acetate/heptane: 1/1) in order to produce 13.5 g (66%) of a white solid, m.p. 125° C.

NMR $^1$H (DMSO): 4.74 (s, 2H); 7,5–8.2 (m, 4H); 8.28 (s, 1H).

4.c. 4-(2-Ethyl-1,3-dioxan-2-yl)-1,2-dihydro-2-pyridinone:

The water is distilled azeotropically for 16 hours with a Dean-Stark apparatus, from a mixture of 1-(2-oxo-1,2-dihydro4-pyridinyl)-1-propanone (obtained according to 1.g, g, 198 mmol), ethylene glycol (60 ml) and p-toluenesulphonic acid (750 mg) in toluene (450 ml). The solvent is then evaporated off under reduced pressure, the residue is taken up in ethyl acetate (300 ml), washed with saturated aqueous sodium bicarbonate (100 ml) and with water. The organic phase is dried and concentrated. The residue is purified by column chromatography (SiO$_2$, methanol/dichloromethane: 5/95 to 7/93) in order to produce 28 g (67%) of a white solid, m.p. 166° C.

NMR $^1$H (CDCl$_3$): 0.86 (t, 3H); 1.32 (m, 1H); 1.69 (q, 2H); 2.10 (m, 1H); 3.82 (m, 4H); 6.35 (dd, 1H); 6.64 (d, 1H); 7.41 (d, 1H); 13.4 (br, 1H).

4.d. 1-(2-Chloro-3-quinolylmethyl)4-(2-ethyl-1,3-dioxan-2-yl)-1,2-dihydro-2-pyridinone:

A solution under argon of 4-(2-ethyl-1,3-dioxan-2-yl)-1,2-dihydro-2-pyridinone (obtained according to 4.e, 11 g, 52 mmol) in anhydrous tetrahydrofuran (370 ml) is treated at 0° C. with sodium hydride (80% in mineral oil, 1.68 g, 56 mmol). The resulting-mixture is maintained under agitation at 0° C. for 15 min then treated with 3-bromomethyl-2-chloroquinoline (obtained according to 4.b, 13.4 g, 52 mmol) and the resulting mixture is maintained under agitation at ambient temperature for 24 hours. The reaction medium is then poured into an aqueous solution saturated in ammonium chloride (400 ml), the phases are separated, and the aqueous phase aqueuse is extracted with dichloromethane. The combined organic phases are washed with saturated aqueous sodium chloride, dried over magnesium sulphate and concentrated under reduced pressure. The residue taken up in diethyl ether forms a precipitate which is collected by filtration and dried in order to produce 13.8 g (69%) of a white solid.

NMR $^1$H (CDCl$_3$): 0.87 (t, 3H); 1,2–1.4 (m, 1H); 1.73 (q, 2H); 1,9–2.2 (m, 1H); 3,6–4.0 (m, 4H); 5.39 (s, 2H); 6.26 (d, 1H); 6.33 (d, 1H); 6.70 (d, 1H); 7,3–8.2 (m, 4H); 8.27 (s, 1H).

4.e. 1-(4-oxo-4,6-Dihydroindolizino[1,2-b]quinoline-2-yl)-1-propanone:

A mixture of 1-(2-chloro-3-quinolylmethyl)4-(2-ethyl-1,3-dioxan-2-yl)-1,2-dihydro-2-pyridinone (obtained according to 4.d, 13.8 g, 36 mmol), tetrabutylammonium bromide (23.2 g, 72 mmol), potassium acetate (5.6 g, 72 mmol), triphenylphosphine (3.77 g, 14 mmol) and palladium acetate (1.57 g, 7 mmol) in anhydrous acetonitrile (300 ml) is heated at 80° C. under an argon atmosphere for 16 hours. The reaction medium is left to cool down to ambient temperature and the precipitate is collected by filtration and washed successively with acetone, with water, with acetonitrile and with diethyl ether in order to produce after drying a white solid (6.2 g). This is treated with trifluoroacetic acid (60 ml) and water (20 ml) at ambient temperature for 1 hour. The acid and the water are driven off by azeotropic distillation with toluene and the residue is suspended in diethyl ether in order to produce after filtration and drying 4.3 g (41%) of a white solid, m.p. >275° C.

NMR $^1$H (CDCl$_3$): 1.27 (t, 3H); 3.03 (q, 2H); 5, 28 (s, 2H); 7.19 (d, 1H); 7,6–8.0 (m, 4H); 8.23 (d, 1H); 8.36 (s, 1H).

4.f. 2-(2-Ethyl-2-oxiranyl)-4,6-dihydroindolizino[1,2-b]quinoline-4-one:

A solution of 1-(4-oxo-4,6-dihydroindolizino[1,2-b]quinoline-2-yl)-1-propanone (obtained according to 4.e, 1.74 g, 6 mmol) and trimethylsulphonium iodide (2.45 g, 12 mmol) in anhydrous dimethylsulphoxide (30 ml) at 13° C. is placed under an argon atmosphere and treated dropwise with a solution of potassium tert-butylate (1.34 g, 12 mmol) in anhydrous dimethylsulphoxide (8 ml). The resulting mixture is agitated for min at ambient temperature. The reaction medium is poured into a 20% aqueous solution of acetic acid (50 ml) and extracted with dichloromethane (2×50 ml). The combined organic fractions are washed with water and with saturated aqueous sodium chloride, dried over magnesium sulphate, treated with activated carbon, filtered and concentrated under reduced pressure. The residue taken up in diethyl ether forms a precipitate which is collected by filtration and washed with diethyl ether in order to produce after drying 1.23 g (67%) of a white solid, m.p. 232° C.

NMR $^1$H (DMSO): 0.92 (t, 3H); 1.77 (m, 1H); 2.34 (m, 1H); 2.83 (d, 1H); 3.15 (d, 1H); 5.22 (s, 2H); 6.56 (s, 1H); 7.14 (s, 1H); 7.70 (t, 1H); 7.85 (t, 1H); 8.06 (d, 1H); 8.11 (d, 1H); 8.67 (s, 1H).

4.g. 3-Hydroxy-3-(4-oxo-4,6-dihydroindolizino[1,2-b]quinoline-2-yl)pentanitrile:

A solution under argon of diethylaluminium chloride (molar solution in dichloromethane, 1.35 ml, 1.35 mmol) and trimethylsilyl cyanide (0.36 ml, 2.7 mmol) in anhydrous dichloromethane (12 ml) is treated at 7° C. with a solution of 2-(2-ethyl-2-oxiranyl)-4,6-dihydroindolizino[1,2-b]quinoline-4-one (obtained according to 4.f, 410 mg, 1.35 mmol) in anhydrous dichloromethane (26 ml) and the resulting mixture is agitated for 48 hours at ambient temperature. The reaction medium is poured into an aqueous solution saturated in ammonium chloride (50 ml) and extracted with dichloromethane (2×25 ml). The combined organic fractions are washed with water and with saturated aqueous sodium chloride, dried over magnesium sulphate, filtered and concentrated under reduced pressure. The residue is purified by column chromatography (SiO$_2$, methanol/dichloromethane: 6/94) in order to produce 122 mg (27%) of a white solid, m.p. 282° C.

NMR $^1$H (DMSO): 0.75 (t, 3H); 1.85 (m, 1H); 1.94 (m, 1H); 3.15 (dd, 1H); 5.23 (s, 2H); 5.91 (s, 1H); 6.70 (d, 1H); 7.35 (d, 1H); 7.70 (t, 1H); 7.86 (t, 1H); 8.14 (m, 2H); 8.67 (s, 1H).

Example 5 tert-Butyl 3-Hydroxy-3-(4-oxo-4,6-dihydroindolizino[1,2-b]quinoline-2-yl)pentanoate A solution of diisopropylamine (0.79 ml, 6 mmol) in anhydrous tetrahydrofuran (12 ml) is treated dropwise at 0° C., under argon, with n-butyllithium (1.6 M in hexane, 3.75 ml, 6 mmol). The resulting mixture is agitated at 0° C. for 15 min, then cooled down to −78° C. and treated with tert-butyl acetate (0.81 ml, 6 mmol). After agitation at −78° C. for 15 min, the resulting lithiated reagent is treated dropwise with a solution of 1-(4-oxo-4,6-dihydroindolizino[1,2-b]quinoline-2-yl)-1-propanone (obtained according to 4.e, 870 mg, 3 mmol) in anhydrous tetrahydrofuran (10 ml) and the resulting mixture is maintained at −78° C. for 15 min, then allowed to return to 0° C. for 1 hour. The reaction medium is hydrolyzed by the addition of an aqueous solution saturated in ammonium chloride (60 ml) and the resulting mixture is extracted with ethyl acetate.

The combined organic phases are washed with saturated aqueous sodium chloride, dried over magnesium sulphate and concentrated under reduced pressure. The residue is recrystallized from ethyl alcohol in order to produce 800 mg (66%) of a white solid, m.p. 213° C.

NMR $^1$H (CDCl$_3$): 0.86 (t, 3H); 1.37 (s, 9H); 1.85 (q, 2H); 2.85 (dd, 2H); 4.64 (s, 1H); 5.26 (s, 2H); 6.82 (s, 1H); 7.42 (s, 1H); 7.65 (t, 1H); 7.82 (t, 1H); 7.92 (d, 1H); 8.22 (d, 1H); 8.37 (s, 1H).

Example 6

3-Hydroxy-3-(4-oxo-4,6-dihydroindolizino[1,2-b]quinoline-2-yl)pentanoic Acid tert-butyl 3-hydroxy-3-(4-oxo-4,6-dihydroindolizino[1,2-b]quinoline-2-yl)pentanoate (obtained according to 5, 750 mg, 1.85 mmol) is treated with trifluoroacetic acid (10 ml) for 1 hour at ambient temperature. The reaction medium is concentrated under reduced pressure, taken up with toluene and concentrated again. The residue, taken up in acetone (10 ml), forms a precipitate which is collected by filtration and washed with acetone in order to produce after drying 450 mg (69%) of a white solid, m.p. 285° C.

NMR $^1$H (DMSO): 0.76 (t, 3H); 1.88 (m, 2H); 2.84 (dd, 2H); 5.22 (s, 2H); 6.62 (s, 1H); 7.29 (s, 1H); 7.70 (t, 1H); 7.85 (t, 1H); 8.11 (d, 1H); 8.15 (d, 1H); 8.66 (s, 1H); 12.1 (br, 1H).

Example 7

3-(9-Benzyloxy-10-fluoro-4-oxo-4,6-dihydroindolizino[1,2-b]quinoline-2-yl)-3-hydroxypentanoic Acid The procedure of Example 6 is applied, replacing the tert-butyl 3-hydroxy-3-(4-oxo-4,6-dihydroindolizino[1,2-b]quinoline-2-yl)pentanoate with tert-butyl 3-(9-benzyloxy-10-fluoro-4-oxo-4,6-dihydroindolizino[1,2-b]quinoline-2-yl)-3-hydroxypentanoate (obtained according to 1). A yellow solid is obtained, m.p. 268° C.

NMR $^1$H (DMSO): 0.73 (t, 3H); 1.86 (m, 2H); 2.84 (dd, 2H); 5.20 (s, 2H); 5.30 (s, 1H); 5.37 (s, 2H); 6.60 (s, 1H); 7.22 (s, 1H); 7,3–7.7 (m, 5H); 7.87 (d, 1H); 7.95 (d, 1H); 8.55 (s, 1H); 12.14 (br, 1H).

Example 8

3-(10-fluoro-9-methoxy-4-oxo-4,6-dihydro-indolizino[1,2-b]quinoline-2-yl)-3-hydroxypentanoic Acid The procedure of Example 6 is applied, replacing the tert-butyl 3-hydroxy-3-(4-oxo-4,6-dihydroindolizino[1,2-b]quinoline-2-yl)pentanoate with tert-butyl 3-(10-fluoro-9-methoxy-4-oxo-4,6-dihydroindolizino[1,2-b]quinoline-2-yl)-3-hydroxy-pentanoate obtained according to 2). A white solid is obtained; m.p.>250° C.

NMR $^1$H (DMSO): 0.74 (t, 3H); 1.86 (m, 2H); 2.84 (dd, 2H); 4.03 (s, 3H); 5.19 (s, 2H); 5.29 (br, 1H); 6.35 (s, 1H); 7.22 (s, 1H); 7.74 (d, 1H); 7.92 (d, 1H); 8.56 (s, 1H); 12.1 (br, $^1$H).

Example 9

3-Hydroxy-3-(7-methyl4-oxo4,6-dihydroindolizino[1,2-b]quinoline-2-yl)pentanoic Acid The procedure of Example 6 is applied, replacing the tert-butyl 3-hydroxy-3-(4-oxo-4,6-dihydroindolizino[1,2-b]quinoline-2-yl)pentanoate with tert-butyl 3-hydroxy-3-(7-methyl-4-oxo-4,6-dihydroindolizino[1,2-b]quinoline-2-yl)pentanoate (obtained according to 3). A white solid is obtained; m.p.>250° C.

NMR $^1$H (DMSO): 0.73 (t, 3H); 1.86 (m, 2H); 2.77 (s, 3H); 2.84 (dd, 2H); 5.22 (s, 2H); 6.61 (s, 1H); 7.26 (s, 1H); 7.72 (t, 1H); 7.84 (t, 1H); 8.14 (d, 1H); 8.25 (d, 1H); 12.1 (br, 1H).

Example 10

3-(9-Benzyloxy-4-oxo-4,6-dihydroindolizino[1,2-b]quinoline-2-yl)-3-hydroxypentanoic Acid The procedures of Examples 1.i, 1.j and 6 are applied, replacing the 6-benzyloxy-7-fluoro-2-iodo-3-quinolylmethanol with 6-benzyloxy-2-iodo-3-quinolylmethanol (obtained according to the method described in Patent Application PCT/FR96/00980). A white solid is obtained; m.p. 278° C. with phase transition at 180° C.

NMR $^1$H (DMSO): 0.74 (t, 3H); 1.87 (m, 2H); 2.84 (dd, 2H); 5.19 (s, 2H); 5.29 (s, 3H); 6.59 (s, 1H); 7.22 (s, 1H); 7,3–7.7 (m, 7H); 8.07 (d, 1H); 8.51 (s, 1H); 12.13 (br, 1H).

Example 11

3-(10-Chloro-9-methyl-4-oxo-4,6-dihydro-indolizino[1,2-b]quinoline-2-yl)-3-hydroxypentanoic Acid The procedures of Examples 1.a, 1.b, 1.e, 1.f, 1.i, 1.j and 6 are applied starting with 3-chloro-4-methylaniline instead of 3-fluoro4-methoxyaniline. A light beige solid is obtained, m.p. >250° C.

NMR $^1$H (DMSO): 0.73 (t, 3H); 1.86 (m, 2H); 2.53 (s, 3H); 2.84 (dd, 2H); 5.18 (s, 2H); 5.31 (br, 1H); 6.62 (s, 1H); 7.26 (s, 1H); 8.07 (s, 1H); 8.18 (s, 1H); 8.58 (s, 1H); 12.14 (br, 1H).

Example 12

Methyl 3-Hydroxy-3-(4-oxo-4,6-dihydroindolizino[1,2-b]quinoline-2-yl)pentanoate A solution of 3-hydroxy-3-(4-oxo-4,6-dihydroindolizino[1,2-b]quinoline-2-yl)-pentanoic acid (obtained according to the procedure of Example 6, 175 mg, 0.5 mmol) and methyl iodide (0.06 ml, 1 mmol) in dimethylsulphoxide is treated dropwise with aqueous soda (1N, 0.5 ml, 0.5 mmol) and the resulting mixture is agitated for 1 hour at ambient temperature. The reaction medium is poured into ice cold water (25 ml), extracted with dichloromethane (2×25 ml), the combined organic fractions are washed with saturated aqueous sodium chloride, dried over magnesium sulphate and concentrated under reduced pressure. The residue taken up in diethyl ether forms a precipitate which is collected by filtration and washed with diethyl ether in order to produce after drying 100 mg (55%) of a white solid, m.p.>250° C.

NMR $^1$H (DMSO): 0.74 (t, 3H); 1.89 (m, 2H); 2.93 (dd, 2H); 3.50 (s, 3H); 5.23 (s, 2H); 5.36 (s, 1H); 6.62 (s, 1H); 7.29 (s, 1H); 7.72 (t, 1H); 7.86 (t, 1H); 8.13 (m, 2H); 8,76 (s, 1H).

Example 13 tert-Butylcarbonyloxy-methyl 3-Hydroxy-3-(4-oxo-4,6-dihydroindolizino[1,2-b]quinoline-2-yl)pentanoate A solution under argon of 3-hydroxy-3-(4-oxo-4,6-dihydroindolizino[1,2-b]quinoline-2-yl)pentanoic acid (obtained according to 6, 175 mg, 0.5 mmol) and potassium carbonate (100 mg, 0.75 mmol) in N,N-dimethylformamide (10 ml) is treated dropwise with chloromethyl pivalate (0.14 ml, 1 mmol) and the resulting mixture is agitated for 24 hours at ambient temperature. The reaction medium is poured into water (25 ml), extracted with ethyl acetate (3×25 ml), the combined organic fractions are washed with saturated aqueous sodium chloride, dried over magnesium sulphate and concentrated under reduced pressure. The residue, taken up in diethyl ether, forms a precipitate which is collected by filtration and washed with diethyl ether in order to produce after drying 110 mg (47%) of a white solid, m.p. 192° C.

NMR $^1$H (DMSO): 0.74 (t, 3H); 1.02 (s, 9H); 1.88 (m, 2H); 2.99 (dd, 2H); 5.21 (s, 2H); 5.35 (s, 1H); 5.58 (dd, 2H), 6.62 (s, 1H); 7.30 (s, 1H); 7.70 (t, 1H); 7.85 (t, 1H); 8.11 (d, 1H); 8.15 (d, 1H); 8.67 (s, 1H).

Example 14

2-[1-Hydroxy-1-(1H-1,2,3,4-tetrazo-5-ylmethyl)propyl]-4,6-dihydroindolizino[1,2-b]quinoline-4-one A solution under argon of 3-hydroxy-3-(4-oxo-4,6-dihydroindolizino[1,2-b]quinoline-2-yl)pentanitrile (obtained according to the procedure of Example 4, 70 mg, 0.21 mmol), of trimethylsilyl nitride (0.083 ml, 0.63 mmol) and of a catalytic quantity of dibutyltin oxide (5 mg) in toluene (5 ml) is heated to reflux for 2 hours. The resulting mass, which resembles gum, is treated with trimethylsilyl nitride (1 ml) and 1,2-dichloroethane (2 ml). The solution obtained is agitated for 1 hour at temperature then concentrated under reduced pressure. The residue, taken up in diethyl ether, forms a precipitate which is collected by filtration and purified by column chromatography ($SiO_2$, acetic acid/methanol/dichloromethane: 0.5/10/90) in order to produce 30 mg (38%) of a white solid, m.p.>250° C.

NMR $^1$H (DMSO): 0.79 (t, 3H); 1.87 (m, 1H); 1.99 (m, 1H); 3.42 (dd, 2H); 5.18 (s, 2H); 5.73 (br, 1H); 6.54 (d, 1H); 7.27 (d, 1H); 7.70 (t, 1H); 7.85 (t, 1H); 8.11 (d, 1H); 8.16 (d, 1H); 8.65 (s, 1H); 12.5 (br, 1H).

Pharmacological Study of the Products of the Invention

1. Inhibition test of the relaxation of supercoiled DNA induced by topoisomerase I.

Supercoiled plasmidic DNA (pUC 19, Pharmacia Biotech, Orsay, France, 300 ng) is incubated at 37° C. for 15 min in the presence of calf thymus topoisomerase I (Gibco-BRL, Paisley, United Kingdom, 1 unit) in 20 μl of reaction buffer (Tris-HCl pH 7.5:50 mM, KCl: 50 mM, DTT: 0.5 mM, $MgCl_2$: 10 mM, EDTA: 0.1 mM, bovine serum albumin: 0.030 mg/ml) and of a potentiel inhibitor (prepared in a 50 mM extemporaneous solution in dimethylsulphoxide, then diluted with distilled water in order to obtain a final concentration of 500 μM, 200 μM, 100 μM or 10 μM, not exceeding 1% of dimethylsulphoxide). The reaction is stopped by the addition of 3 μl of a denaturing solution (proteinase K: 500 μg/ml, sodium dodecylsulphate: 1%, EDTA: 20 mM) followed by incubation at 37° C. for 30 min, then 2 μl of a loading buffer (bromophenol blue: 0.3%, sodium hydrogen phosphate: 10 mM, polysucrose Ficoll®-400: 16%) are added and the sample is placed on a 1.2% agarose gel (Sea-Kem-GTG, FMC Bioproducts/Tebu, Perray-en-Yvelines, France) containing 2 μg/ml of chloroquine. The electrophoretic migration is carried out at a voltage of 1V/cm for 20 hours, with recirculation of the electrophoresis buffer (Tris-HCl: 36 mM, sodium dihydrogen phosphate: 30 mM, EDTA: 1 mM). The gel is then stained under agitation with 2 μg/ml ethidium bromide, then photographed under ultraviolet light at 312 nm (CCD camera Vilber-Lourmat, Lyon, France). Densitometric analysis (BioProfil image analyzer Vilber-Lourmat, Lyon, France) allows the percentage of relaxed DNA with respect to total DNA to be expressed, at the chosen concentration of inhibitor. The results are set out in Table I below for the compound of general formula (I) corresponding to Example 6. It appears that at concentrations greater than 10 μM, the compound of Example 6 is a better inhibitor of topoisomerase I than camptothecin, a known inhibitor of topoisomerase I.

TABLE I

| | PERCENTAGE OF RELAXED DNA | | | |
| --- | --- | --- | --- | --- |
| | CONCENTRATION (μM) | | | |
| Compound | 10 | 100 | 200 | 500 |
| Camptothecin | 95.5 ± 1.4 | 64.2 ± 6.1 | 60.6 ± 12.0 | 55.6 ± 8.8 |
| Example 6 | 95.2 ± 2.8 | 28.5 ± 3.5 | 15.5 ± 3.6 | 10.3 ± 2.8 |

2. Inhibition test of the relaxation of supercoiled DNA induced by topoisomerase II.

Supercoiled plasmidic DNA (pUC 19, Pharmacia Biotech, Orsay, France, 300 ng) is incubated at 37° C. for 15 min in the presence of calf thymus topoisomerase I (Gibco-BRL, Paisley, United Kingdom, 7 units) in 20 μl of reaction buffer (Tris-HCl pH 7.9: 10 mM, KCl: 50 mM, NaCl: 50 mM, $MgCl_2$: 5 mM, ATP: 1 mM, EDTA: 100 mM, bovine serum albumin: 15 mg/ml) and of a potential inhibitor (prepared in a 50 mM extemporaneous solution in dimethylsulphoxide, then diluted with distilled water in order to obtain a final concentration of 500 μM, 200 μM, 100 μM or 10 μM, not exceeding 1% of dimethylsulphoxide). The reaction is stopped by the addition of 3 μl of a denaturing solution (proteinase K: 500 μg/ml, sodium dodecylsulphate: 1%, EDTA: 20 mM) followed by incubation at 37° C. for 30 min, then 2 μl of a loading buffer (bromophenol blue: 0.3%, sodium hydrogen phosphate: 10 mM, polysucrose Ficoll®-400: 16%) are added and the sample is placed on a 1.2% agarose gel (Sea-Kem-GTG, FMC Bioproducts/Tebu, Perray-en-Yvelines, France) containing 2 μg/ml of chloroquine. The electrophoretic migration is carried out at a voltage of 1V/cm for 20 hours, with recirculation of the electophoresis buffer (Tris-HCl: 36 mM, sodium dihydrogen phosphate: 30 mM, EDTA: 1 mM). The gel is then stained under agitation with 2 μg/ml ethidium bromide, then photographed under ultraviolet light at 312 nm (CCD camera Vilber-Lourmat, Lyon, France). Densitometric analysis (BioProfil image analyzer Vilber-Lourmat, Lyon, France) allows the percentage of relaxed DNA with respect to the total DNA to be expressed, at the chosen concentration of inhibitor. The results are set out in Table II below for the compound of general formula (I) corresponding to Example 6. It appears that at concentrations greater than 10 μM, the compound of Example 6 is a better inhibitor of topoisomerase II than etoposide, a known inhibitor of topoisomerase II.

TABLEAU II

| | PERCENTAGE OF RELAXED DNA | | | |
| --- | --- | --- | --- | --- |
| | CONCENTRATION (μM) | | | |
| Compound | 10 | 100 | 200 | 500 |
| Etoposide | 92.6 ± 2.5 | 28.5 ± 2.2 | 18.6 ± 1.4 | 12.0 ± 0.8 |
| Example 6 | 98.8 ± 0.4 | 9.9 ± 0.7 | 11.5 ± 1.9 | 6.5 ± 1.0 |

What is claimed is:

1. A compound of the formula

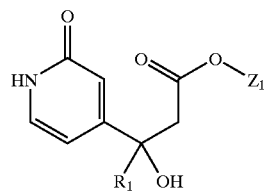

A wherein $R_1$ is selected from the group consisting of alkyl of 1 to 6 carbon atoms, alkenyl of 2 to 6 carbon atoms, alkynyl of 2 to 6 carbon atoms, haloalkyl of 1 to 6 carbon atoms, alkoxy alkyl of 1 to 6 alkoxy carbon atoms and 1 to 6 alkyl carbon atoms and alkylthioalkyl of 1 to 6 carbon atoms for each alkyl and $Z_1$ is alkyl of 1 to 6 carbon atoms.

2. A process for the preparation of a compound of claim 1 comprising reacting a 2-alkoxypyridine of the formula

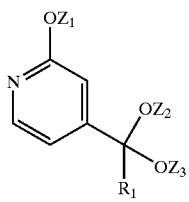

J wherein $R_1$ and $Z_1$ are defined as in claim 24 and $Z_2$ and $Z_3$ are independently alkyl of 1 to 6 carbon atoms or together form a saturated hydrocarbon of 2 to 4 carbon atoms is deprotected to form a compound of the formula

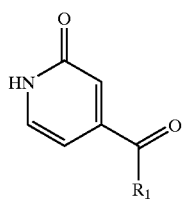

K and reacting the said compound with a alkylation agent to form the compound of claim 1.

3. A compound of the formula

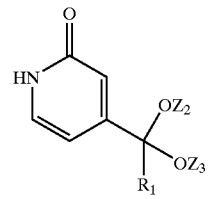

D wherein $R_1$ is selected from the group consisting of alkyl of 1 to 6 carbon atoms, alkenyl of 2 to 6 carbon atoms, alkynyl of 2 to 6 carbon atoms, haloalkyl of 1 to 6 carbon atoms, alkoxy alkyl of 1 to 6 alkoxy carbon atoms and 1 to 6 alkyl carbon atoms and alkylthioalkyl of 1 to 6 carbon atoms for each alkyl and $Z_1$ is alkyl of 1 to 6 carbon atoms and $Z_2$ and $Z_3$ are independently alkyl of 1 to 6 carbon atoms or taken together form a saturated hydrocarbon of 2 to 4 carbon atoms.

4. A process for the preparation of a compound of claim 3 comprising reacting a compound of the formula

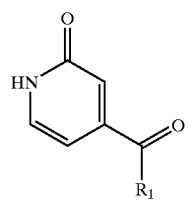

K with a keto protecting group to obtain the compound of claim 3.

5. A compound of the formula

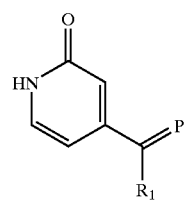

K wherein $R_1$ is selected from the group consisting of alkenyl of 2 to 6 carbon atoms, alkynyl of 2 to 6 carbon atoms, haloalkyl of 1 to 6 carbon atoms, alkoxy alkyl of 1 to 6 carbon atoms and 1 to 6 alkyl carbon atoms and alkylthioalkyl of 1 to 6 carbon atoms for each alkyl.

* * * * *